United States Patent [19]

Grimmer et al.

[11] Patent Number: 5,095,115
[45] Date of Patent: Mar. 10, 1992

[54] PREPARATION OF RIBOFLAVIN 5'-PHOSPHATE (FMN) AND ITS SODIUM SALT IN A LACTONE

[75] Inventors: Johannes Grimmer, Ludwigshafen; Hans Kiefer, Wachenheim, both of Fed. Rep. of Germany

[73] Assignee: BASF Aktiengesellschaft, Ludwigshafen, Fed. Rep. of Germany

[21] Appl. No.: 571,230

[22] Filed: Aug. 23, 1990

[30] Foreign Application Priority Data

Sep. 14, 1989 [DE] Fed. Rep. of Germany ....... 3930668

[51] Int. Cl.5 ............................................. C07F 9/6561
[52] U.S. Cl. ...................................... 544/244; 544/251
[58] Field of Search ................................. 544/244, 251

[56] References Cited

U.S. PATENT DOCUMENTS

| | | | |
|---|---|---|---|
| 2,111,491 | 3/1938 | Kuhn et al. | 544/251 |
| 2,610,176 | 9/1952 | Flexser et al. | 544/244 |
| 2,610,177 | 9/1952 | Flexser et al. | 544/251 |
| 4,987,229 | 1/1991 | Dobler et al. | 544/244 |

FOREIGN PATENT DOCUMENTS

| | | | |
|---|---|---|---|
| 364875 | 4/1990 | European Pat. Off. | 544/244 |
| 687980 | 2/1953 | United Kingdom | 544/244 |
| 690463 | 4/1953 | United Kingdom | 544/244 |
| 1102399 | 2/1968 | United Kingdom | 544/244 |

OTHER PUBLICATIONS

Abstract for JP 008836 (3/14/72).
Derwent Abstract for JP008554 (3/11/72).
Derwent Abstract for JP008836 (3/14/72).
Tanaka et al, *Chemical Abstracts*, vol. 79, No. 146560 (1973).
Chemical Engineering, pp. 120–121 (Nov. 1954).
Kumagai et al, Chemical Abstracts, vol. 83, Nos. 79549–79551 (1975).
Abstract for JP 008554 (3/11/72).

*Primary Examiner*—Nicholas S. Rizzo
*Assistant Examiner*—E. Bernhardt
*Attorney, Agent, or Firm*—Oblon, Spivak, McClelland, Maier & Neustadt

[57] ABSTRACT

An improved process for preparing riboflavin 5'-phosphate (FMN) or its monosodium salt by reacting riboflavin with excess phosphorus oxychloride in a solvent, hydrolyzing of the resulting reaction mixture and, if desired, partially neutralizing with aqueous sodium hydroxide solution, comprises reacting the riboflavin with from 1.2 to 3 moles of phosphorus oxychloride per mole of riboflavin in a suitable lactone, especially γ-butyrolactone, as solvent. The process is particularly advantageous when the reaction mixture is hydrolyzed at from 80° to 90° C. continuously or batchwise.

8 Claims, No Drawings

PREPARATION OF RIBOFLAVIN 5'-PHOSPHATE (FMN) AND ITS SODIUM SALT IN A LACTONE

The present invention relates to an improved process for preparing riboflavin 5'-phosphate (flavin mononucleotide and thus called FMN hereinafter) and for preparing the monosodium salt of FMN, which is the usual commercial product, of the formula I

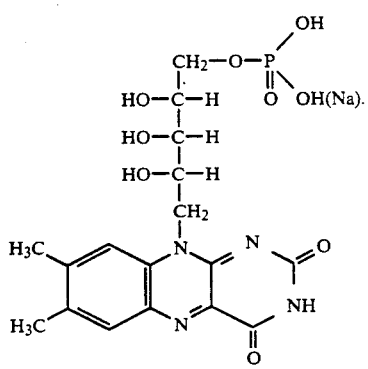

FMN is essential as a coenzyme in various enzymic reactions in the body and is therefore used in the form of its salts, especially in the form of sodium FMN, as additive to drugs and human and animal food. Sodium FMN is also used as starting material for flavin adenine dinucleotide which is employed for treating vitamin $B_2$ deficiency.

Sodium FMN is generally prepared by direct reaction of riboflavin with a phosphorylating agent such as phosphorus oxychloride, which may be partially hydrolyzed, in an organic solvent. Selective phosphorylation is not straightforward. Thus, for example, the process of U.S. Pat. No. 2,610,177 uses an approximately 20-fold molar excess of partially hydrolyzed phosphorus oxychloride. The disadvantages of this process are, besides the use of such large quantities of phosphorus oxychloride and the environmental pollution associated therewith, the fact that the resulting product still contains considerable quantities of unreacted riboflavin as well as isomeric mono- and polyphosphates as by-products. This is why the FMN must be purified in a way which is technically very complicated in order to obtain products which meet the purity criteria of USP and the European Pharmacopoeia. This entails the crude product being dissolved in the form of monoammonium salts by treatment several times with ethanolamine or morpholine and being separated from unreacted and undissolved riboflavin. This purification operation is also described in Chemical Engineering, Nov. 1954, pages 120 et seq.

The phosphorylation with $POCl_3$ described in U.S. Pat. No. 2,111,491 takes place in a very large excess of pyridine. The disadvantages of this process, besides the use of such large quantities of toxic pyridine, which is used reluctantly because of its unpleasant odor, are that the product is impure and the working up is very complicated.

The phosphorylation of riboflavin with a small excess of $POCl_3$ in solvents such as tetrahydrofuran, diethylene glycol dimethyl ether, monoethylene glycol dimethyl ether, triethyl phosphate, 1,2-dichloroethane and 1,2-dibromoethane is described in C.A. 83 (1975) 79549f, 79550z and 79551a (JP-A 25597/1975, JP-A 25598/1975 and JP-A 25596/1975 respectively). As is shown by Comparative Examples 1 to 8, repetition of the said processes reveals that little or no FMN is formed under the reaction conditions indicated in these citations. The high yields of FMN indicated in these citations are probably based on an error arising from the great difficulty at that time in analyzing this class of compounds.

It is evident from the use of large quantities of phosphorus oxychloride for the phosphorylation of riboflavin (vitamin $B_2$) that processes of this type may have a considerable effect on the chloride load of waste water. The economics and environmental acceptability of the process are not improved by the purification of vitamin $B_2$ phosphate by absorption on a cellulose ion exchanger and elution with a sodium oxalate/oxalic acid or ammonium formate/formic acid buffer (cf. JP-B 47/8836 and JP-B 47/8554) because the amounts of buffer salts are too large for industrial use.

Hence it was an object of the present invention to develop a process for preparing FMN or its monosodium salt in which the disadvantages of the prior art are avoided, ie. in which FMN and its sodium salt are prepared in a straightforward and environmentally acceptable manner and in a purity meeting Pharmacopeia requirements.

We have now found, surprisingly, that FMN and its salts are obtained in a particularly advantageous manner when the phosphorylation of riboflavin is carried out with $POCl_3$ in a lactone, especially in γ-butyrolactone, as solubilizer. The initial product in this reaction is cyclic riboflavin 4',5'-phosphochloridate of the formula III, which can be isolated by precipitation with a suitable agent such as methyl tert-butyl ether. However, the compound of the formula III does not have to be isolated because Na FMN can be obtained from it in a commercial form in a single step. The equation below represents the reaction:

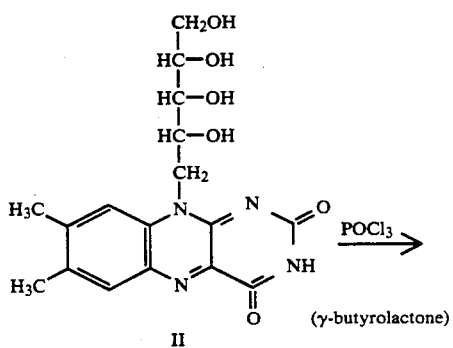

-continued

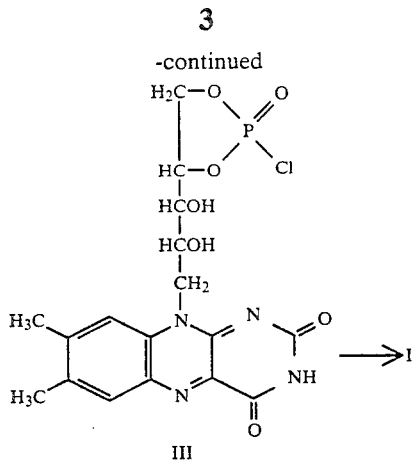

It was also surprising that the lactone is not attacked by the phosphorylating agent in the reaction of vitamin B₂ with POCl₃ and, furthermore, that it suffers no adverse effects under the drastic hydrolysis conditions. It is perfectly suitable for re-use as solvent for the next phosphorylation after it has been extracted from the aqueous filtrate from which the Na FMN has been isolated.

The present invention therefore relates to a process for preparing riboflavin 5'-phosphate or its monosodium salt by reacting riboflavin with excess phosphorus oxychloride in a solvent, treating the reaction mixture with water and, if desired, subsequently partly neutralizing the resulting riboflavin monophosphate with aqueous sodium hydroxide solution, which comprises carrying out the reaction of the riboflavin with 1.2 to 3 moles of phosphorus oxychloride per mole of riboflavin in a lactone such as γ-butyrolactone, γ-decalactone or γ-valerolactone. γButyrolactone is particularly important as solvent because, on the one hand, it can be used very advantageously and, on the other hand, it is commercially available in sufficient quantity. Furthermore, the acute toxicity of γ-butyrolactone is low and, in the body, it is rapidly metabolized via γ-hydroxybutyric acid and thus mostly exhaled in the form of CO₂ (cf. Toxikolog. Bewertungen, No. 7, edition 02/89, page 1, Berufsgenossenschaft der Chemischen Industrie Heidelberg).

The lactone is generally used in amounts of from 1 to 3 l, preferably about 1 to 1.5 l, per mole of riboflavin.

Particularly good yields are obtained in the process according to the invention when the reaction mixture obtained from the phosphorylation and containing the novel cyclic riboflavin 4',5'-phosphochloridate of the formula III is treated with water at from about 70° to 90° C., preferably 80° to 90° C.

An advantageous procedure for the process according to the invention is such that the lactone is initially introduced, riboflavin and POCl₃ are added to it, and the reaction mixture is slowly heated to about 30° to 35° C. and then stirred at this temperature until the formation of the phosphochloridate of the formula III is complete. This reaction generally takes from about 15 to 60 minutes, preferably about 30 to 60 minutes. The reaction mixture becomes a dark homogeneous solution after about 30 minutes. This phosphorylation can be carried out at from 20° to 50° C., preferably 30° to 35° C.

The subsequent hydrolysis of the phosphochloridate of the formula III to give FMN can be carried out in a variety of ways, batchwise or continuously.

For the batchwise procedure, for example the reaction mixture obtained from the phosphorylation is heated, while passing in steam and slowly adding deionized water, to from 85° to 90° C. and subsequently maintained at from 85° to 95° C. for about 5 to 20, preferably about 10–15, minutes.

The amount of water used for this is generally from 30 to 50 moles, preferably 35 to 40 moles, per mole of riboflavin.

The isomerization to the 4'-phosphate which starts during the hydrolysis is stopped by rapidly adding further water. Required for this are about from 60 to 100 moles, preferably 65 to 80 moles, of additional water based on riboflavin employed.

The reaction mixture is cooled to room temperature, and it is then possible to isolate FMN or, after addition of aqueous sodium hydroxide solution, to a pH of about 5.5 to 6, the sodium salt of FMN in a conventional manner.

Accordingly, the invention also relates to the process described above for preparing riboflavin 5'-phosphate or its monosodium salt by reacting riboflavin with 1.2 to 3 moles of POCl₃ in a suitable lactone, in which the reaction mixture obtained from the phosphorylation is heated, while passing in steam and slowly adding from 30 to 50 moles of water per mole of riboflavin, to from 85° to 90° C. and then maintained at from 85° to 95° C. for about 5 to 20 minutes, and the reaction mixture is mixed with a further 60 to 100 moles of water, allowed to cool and, if desired, adjusted to a pH of from 5.5 to 6 with aqueous sodium hydroxide solution.

An advantageous variant of the process according to the invention comprises continuously introducing the reaction mixture obtained from the phosphorylation into about 90 to 150 moles of water, which is at from 80° to 100° C., per mole of riboflavin in such a way that the reaction mixture is at from 80° to 95° C., maintaining the reaction mixture at this temperature for from 1 to 10 minutes, allowing it to cool and, if desired, adjusting the pH to from 5.5 to 6 with aqueous sodium hydroxide solution to prepare the sodium salt.

A very particularly advantageous embodiment of this variant is to heat the reaction mixture obtained from the phosphorylation briefly to from 40° to 65° C., preferably 55° to 60° C., before it is introduced into the hot water.

Another advantageous variant of the process according to the invention comprises mixing the reaction mixture obtained from the phosphorylation with from 30 to 150 moles of water per mole of riboflavin in a heated mixing vessel and, after remaining at from 80° to 95° C. for from 5 to 15 minutes, allowing the mixture to cool and, if desired, adjusting the pH to from 5.5 to 6 with aqueous sodium hydroxide solution to prepare the sodium salt.

Care must be taken in the preparation of FMN or its monosodium salt according to the invention that the reaction mixture containing the cyclic riboflavin 4',5'-phosphochloridate reaches 80° to 95° C. as quickly as possible, and this temperature is maintained for the stated time without falling below 80° C., otherwise a product with an unacceptably high riboflavin content is obtained. In addition, the reaction mixture should not be kept at 95° C. for more than 10 min. The maximum temperature for a longer heating time is 90° C.

The reaction of riboflavin 5'-phosphate with NaOH to give its monosodium salt is generally carried out at from 20° C., preferably 30° to 40° C.

The present invention also relates to the straightforward one-spot process for preparing pure riboflavin 5'-phosphate or its monosodium salt, which comprises A: reacting riboflavin with 1.2 to 3 moles of phosphorus oxychloride per mole of riboflavin in γ-butyrolacetone at from 20° to 50° C., B: treating the resulting reaction mixture which contains the novel cyclic riboflavin 4',5'-phosphochloridate of the formula III with about 30 to 50 moles of water per mole of phosphochloridate at from 70° to 90° C., preferably 80° to 90° C., C: maintaining the reaction mixture at from 80° to 95° C. for from 1 to 15 minutes, D: then adding from 65 to 100 moles of water per mole of riboflavin to the reaction mixture and isolating the riboflavin 5'-phosphate which has crystallized out or, if desired, E: adjusting the reaction mixture obtained from D to a pH of from 5.5 to 6 at from 20° to 50° C., preferably 30° to 40° C., with aqueous NaOH, and isolating the monosodium salt of riboflavin 5'-phosphate which has crystallized out.

The riboflavin 5'-phosphate obtained in the process according to the invention generally contains less than 6% riboflavin and 75 to 80% riboflavin 5'-phosphate and thus meets the purity requirements for pharmaceuticals. No elaborate purification operations are required. A particular advantage of the process is that it is also possible to employ low quality riboflavin (eg. crude riboflavin) because impurities remain in solution.

EXAMPLE 1

180 ml of γ-butyrolactone were placed in a 1 l four-neck flask and, while stirring, 54 g of riboflavin (drugs quality=0.144 mol) and 54 g of phosphorus oxychloride (0.352 mol) were successively introduced. The residues attached to the wall of the flask were washed into the reaction mixture with 36 ml of γ-butyrolactone. The contents of the flask were then slowly heated to 30°-35° C. and stirred at this temperature for 1 h. After about 30 min, the reaction mixture was a homogeneous dark solution. 90 ml of deionized water were then rapidly (in about 1 min) added dropwise and, during this, steam was passed in to raise the temperature steadily from 35° C. to a maximum of 90° C. The reaction mixture was then maintained at from 85° to 90° C. for 10 min while adding a further 126 ml of deionized water and passing in steam. The isomerization was then stopped by pumping in a further 216 ml of deionized water. The contents of the flask were subsequently cooled to 20° to 25° C. and finally 315 ml of a 25% strength aqueous sodium hydroxide solution were added, resulting in a pH of about 5.5 and a temperature of about 30° C. The mixture was then cooled to room temperature (RT), stirred for 1 h and filtered through a G2 sintered glass disk to remove the riboflavin 5'-phosphate sodium. By-products were removed form the desired product by washing with about 450 ml of a 60:40 mixture of methanol and deionized water and then with 180 ml of pure methanol. The product was sucked dry and, still moist with methanol, made into a paste in about 350 ml of deionized water and then spray-dried.

The yield was 58 g, corresponding to 84% of theory. HPLC analysis showed that the product had the following composition:

5-7% riboflavin 3'-monophosphate
9-11% riboflavin 4'-monophosphate
76-80% riboflavin 5'-monophosphate
4-5.8% free riboflavin

EXAMPLE 2

400 ml of γ-butyrolactone were placed in a 1 l four-neck flask and, while stirring, 120 g of riboflavin (drugs quality) and 120 g of POCl$_3$ in 80 ml of γ-butyrolactone were successively introduced. The mixture was left to react at from 30° to 35° C. for 1 h and then heated to 40° C., and it was then pumped within 10 min into 960 ml of deionized water at 80° C. The maximum temperature during this was 87° C. The reaction mixture was stirred at 87° C. for 6 min and then allowed to cool, when riboflavin 5'-phosphate precipitated at about 57° C. To form the sodium salt, 25% strength aqueous NaOH solution was added slowly at below 40° C. until the pH was 5.5. The reaction mixture was then cooled in an ice bath for about 30 min, and the precipitate was filtered off with suction and washed with 1 l of aqueous methanol. The precipitate was sucked dry and dried to constant weight at 30° C. under reduced pressure.

Yield: 125.7 g, corresponding to 82% of theory, containing according to HPLC analysis 11.3% riboflavin 4'-phosphate
71.4% riboflavin 5'-phosphate
4.5% riboflavin and
5.1% sodium.

The optical rotation of the product (determined by the USP method) was +38.9°.

EXAMPLE 3

120 g of riboflavin (drugs quality) and 120 g of POCl$_3$ were reacted as in Example 2 in 480 ml of γ-butyrolactone at from 30° to 35° C. for 1 h, and then the reaction mixture was heated in a heating bath at 120° C. to about 60° C. and, at this temperature, pumped within 10 in into 960 ml of deionized water at 80° C., during which the maximum temperature was 89° C. The reaction mixture was stirred at 89° C. for 6 min and then worked up as in Example 2 to yield 134.5 g of the monosodium salt of riboflavin, corresponding to 88.2% of theory.

HPLC analysis showed that this product contained 11.1% riboflavin 4'-phosphate
70.6% riboflavin 5'-phosphate
3.7% riboflavin and
4.9% sodium.

The optical rotation (determined by the USP method) was +38.6°.

EXAMPLE 4

132 g of crude riboflavin (riboflavin content 93.5%) and 120 g of POCl$_3$ were reacted as in Example 2 in 480 ml of γ-butyrolactone at from 30° to 35° C. for 1 h, and then the reaction mixture was heated within 1 min to 67° C. in a heating bath at 120° C. and was pumped into 960 ml of deionized water at 80° C., during which the maximum temperature was 89° C. The reaction mixture was stirred at 89° C. for 6 min and then worked up as in Example 2 to yield 126.6 g of the monosodium salt of riboflavin.

HPLC analysis showed that this product contains 11.6% riboflavin 4'-phosphate
71.3% riboflavin 5'-phosphate
4.0% riboflavin and
5.1% sodium.

The optical rotation (determined by the USP method) was +39°.

EXAMPLE 5

132 g of crude riboflavin (riboflavin content 93.5%) were phosphorylated with 120 g of POCl₃ in 480 ml of γ-butyrolactone at from 35° to 37° C. as in Example 2. The reaction mixture was then heated to 40° to 45° C. and further heated to 89° C. while slowly adding deionized water. The mixture was kept at 89° C. for 3 min and was then stirred under the conditions indicated in the table.

To investigate the progress of the reaction, on each occasion 1 drop was removed from the reaction mixture and added to about 3 ml of water at about 95° C., and this sample was kept at 95° C. for 5 min and then mixed with 6 ml of a mixture of 0.1 M aqueous ammonium for-mate solution and methanol (in the ration 4:1 by volume) and investigated by HPLC, eluting with the same mixture.

TABLE

| Comparative Example | Literature | Solvent | [ml] | POCl₃ [ml] | Stirring [h/°C.] | Sampling [after ... h] | Composition of the of the reaction mixture [%] | | | |
|---|---|---|---|---|---|---|---|---|---|---|
| | | | | | | | 5'-phosphate | 4'-phosphate | 3'-phosphate | Riboflavin |
| 1 | JP-B 2559/81 (Example 2) | Triethyl phosphate | 75 | 12.5 | 20/25 | 1 | 2.8 | 0.7 | 0.8 | 92.8 |
| | | | | | | 3 | 9.5 | 2.4 | 2.7 | 77.2 |
| | | | | | | 20 | 41.1 | 10.3 | 11.6 | 22.8 |
| 2 | JP-B 2559/81 (Example 2) | Triethyl phosphate | 80 | 14 | 3/23–27 | 1 | 4.9 | 1.2 | ·1.4 | 87.1 |
| | | | | | | 3 | 12.8 | 3.2 | 1.7 | 70.9 |
| 3 | JP-B 40158/82 | 1,2-Dichloroethane +1,2-dibromoethane | 35 40 | 14 | 20/25 | 20 | — | — | — | 99.6 |
| 4 | JP-B 40158/82 | 1,2-dibromoethane | 61 | 14 | 4.5/23 | 4.5 | 0.22 | — | — | 98.1 |
| 5 | JP-B 40158/82 | 1,2-dichloroethane | 64 | 14 | 68/24 | 68 | — | — | — | 99.9 |
| 6 | JP-B 40157/82 | Diethylene glycol dimethyl ether | 75 | 14 | 2/25 | 2 | — | — | — | 98.4 |
| | | | | | | 90 | 18.7 | — | — | 71.7 |
| 7 | JP-B 40157/82 | Diethylene glycol dimethyl ether +tetrahydrofuran | 20 20 | | 7 | 3 | — | — | — | 97.2 |
| | | | | | | 36 | 4.6 | 1.1 | 1.3 | 89.8 |
| 8 | JP-B 40157/82 | Tetrahydrofuran | 81 | 14 | 18/25 | 18 | — | — | — | 99.2 | at from 68° to 75° C. for 25 min in a water bath. Water was added dropwise at 75° C. to make the total volume added 960 ml. The reaction mixture was worked up as in Example 2 to yield 132.4 g of the monosodium salt of riboflavin. HPLC analysis showed that this product contains 11.6% riboflavin 4'-phosphate
71.7% riboflavin 5'-phosphate
3.9% riboflavin and
4.6% sodium.

The optical rotation (determined by the USP method) was +38.9°.

Comparative Examples 1 to 8

In each case, 19 g of riboflavin (about 99% pure) were suspended by stirring in the solvent indicated in the table in a 500 ml four-neck flask, the amount of phosphorus oxychloride (POCl₃) indicated in the table was added to the suspension at 25° C., and the mixture

We claim:

1. A process for preparing riboflavin 5'-phosphate or its monosodium salt by reacting riboflavin with excess phosphorus oxychloride in a solvent, hydrolyzing the resulting reaction mixture by treatment with water and, for preparing the monosodium salt, partially neutralizing with aqueous sodium hydroxide solution, which comprises reacting the riboflavin with 1.2 to 3 moles of phosphorus oxychloride per mole of riboflavin in a suitable lactone selected from the group consisting of γ-butyrolactone, γ-decalactone, and γ-valerolactone.

2. A process as claimed in claim 1, wherein the riboflavin is reacted with the phosphorus oxychloride in γ-butyrolactone.

3. A process as claimed in claim 1, wherein the resulting reaction mixture is treated with water at about 70° to 90° C.

4. A process as claimed in claim 3, wherein the reaction mixture obtained from the phosphorylation is heated, while passing in steam and slowly adding 30 to 50 moles of water per mole of riboflavin, to 85° to 90° C. and then maintained at 85° to 95° C. for about 5 to 20 minutes, and the reaction mixture is mixed with a further 60 to 100 moles of water, allowed to cool and, for preparing the monosodium salt, adjusted to a pH of 5.5 to 6 with aqueous sodium hydroxide solution.

5. A process as claimed in claim 3, wherein the reaction mixture obtained from the phosphorylation is continuously introduced into about 90 to 150 moles of water, which is at from 80° to 100° C., per mole of riboflavin in such a way that the reaction mixture is at 80° to 95° C., and the reaction mixture is maintained at this temperature for 1 to 10 minutes, is allowed to cool and, for preparing the monosodium salt, adjusted to a pH of 5.5 to 6 with aqueous sodium hydroxide solution to prepare the sodium salt.

6. A process as claimed in claim 3, wherein the reaction mixture obtained from the phosphorylation is briefly heated to 40° to 65° C., the heated solution is introduced continuously into about 90 to 150 moles of water at 80° to 100° C. per mole of riboflavin in such a way that the temperature of the reaction mixture is 80° to 95° C., and the reaction mixture is maintained at this temperature for 1 to 10 minutes, is allowed to cool and, for preparing the monosodium salt, adjusted to a pH of 5.5 to 6 with aqueous sodium hydroxide solution to prepare the sodium salt.

7. A process as claimed in claim 3, wherein the reaction mixture obtained from the phosphorylation is mixed with 30 to 150 moles of water per mole of riboflavin in a heated mixing vessel, and after remaining at 80° to 95° C. for 5 to 15 minutes it is allowed to cool and, for preparing the monosodium, adjusted to a pH of 5.5 to 6 with aqueous sodium hydroxide solution to prepare the sodium salt.

8. A process for preparing pure riboflavin 5'-phosphate or its monosodium salt, which comprises
A: reacting riboflavin with 1.2 to 3 moles of phosphorus oxychloride per mole of riboflavin in γ-butyrolactone at from 20° to 50° C.,
B: treating the resulting reaction mixture which contains the novel cyclic riboflavin 4',5'-phosphochloridate of the formula III

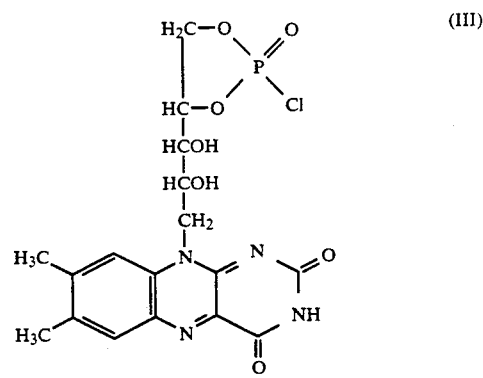

with about 30 to 50 moles of water per mole of phosphochloridate at 70° to 90° C.
C: maintaining the reaction mixture at 80° to 95° C, for 1 to 15 minutes,
D: then adding 65 to 100 moles of water per mole of riboflavin to the reaction mixture and isolating the riboflavin 5'-phosphate which has crystallized out or, for preparing the monosodium salt,
E: adjusting the reaction mixture obtained from D to a pH of 5.5 to 6 at from 20° to 40° C. with aqueous NaOH, and isolating the monosodium salt of riboflavin 5'-phosphate which has crystallized out.

* * * * *